United States Patent [19] … [11] 4,058,548
Olivé et al. … [45] Nov. 15, 1977

[54] PROCESS FOR PREPARING ACETONITRILE

[75] Inventors: Gisela Olivé; Salvador Olivé, both of Zollikerberg, Switzerland

[73] Assignee: Monsanto Company, St. Louis, Mo.

[21] Appl. No.: 692,630

[22] Filed: June 3, 1976

[51] Int. Cl.$^2$ .......................................... C07C 120/00
[52] U.S. Cl. ................................................. 260/465.1
[58] Field of Search ..................................... 260/465.1

[56] References Cited

U.S. PATENT DOCUMENTS

| | | | |
|---|---|---|---|
| 1,684,634 | 9/1928 | Luther et al. | 260/465.1 |
| 2,375,016 | 5/1945 | Marple et al. | 260/465.9 |
| 2,388,218 | 10/1945 | Olin | 260/465.1 |
| 2,849,478 | 8/1958 | Zubey et al. | 260/465.9 X |
| 3,719,701 | 3/1973 | Bach | 260/464 X |
| 3,940,429 | 2/1976 | McConaghy, Jr. et al. | 260/465.9 |
| B 530,925 | 2/1976 | McConaghy, Jr. | 260/465.9 |

OTHER PUBLICATIONS

Emmett, et al.; J.A.C.S., 54, pp. 538–548 (1932).

*Primary Examiner*—Joseph P. Brust
*Attorney, Agent, or Firm*—Joseph D. Kennedy; John D. Upham

[57] ABSTRACT

A process is described for converting methyl amines to acetonitrile by heating with a transition metal catalyst in the presence of hydrogen.

24 Claims, 1 Drawing Figure

U.S. Patent      Nov. 15, 1977      4,058,548
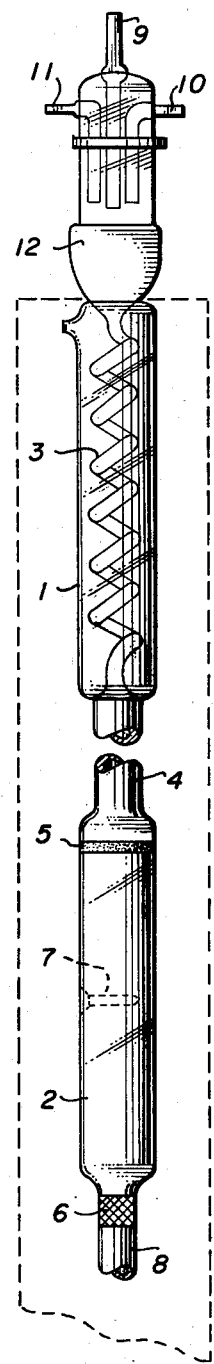

PROCESS FOR PREPARING ACETONITRILE

The present invention relates to a process for preparing acetonitrile by catalytic decomposition of methyl amine at higher temperatures in the presence of hydrogen and of a catalyst.

Acetonitrile is a chemical compound which has recognized utility and considerable industrial potential. Because of its stability under a wide range of conditions it is highly appropriate as a specialty solvent able to dissolve also many inorganic salts or complexes. It is very useful as an intermediate in various syntheses. For example, it can be converted readily to many valuable products such as acids, esters, amines, aldehydes, etc. Acetonitrile can be hydrolyzed to acetamide and acetic acid. The reaction with formaldehyde is of particular interest in view of possible shortage of hydrocarbons, because the total synthesis of acrylonitrile using the acetonitrile produced in accordance with the herein disclosed process of invention can be accomplished with carbon monoxide, ammonia and hydrogen as the sole originally used reactants. Numerous processes for the manufacture of acetonitrile using various starting compounds have been reported in the technical literature. Acetonitrile has been obtained, for example, by:

a. reaction of hydrocarbons, such as methane, ethane, ethylene, acetylene, propane, propylene and isobutylene, or of methanol, with either cyanogen or hydrocyanic acid;

b. ammoxidation (oxidative ammonolysis) of hydrocarbons, such as propane, butane, isobutane, cyclohexene, methylcyclohexene, ethylene, propylene and acetylene, or of hydrocarbon derivates, such as acrolein, ethanol, propanol, isopropanol, acetaldehyde, acetone, ethyl formiate and methyl acetate;

c. dehydration of ammonium acetate or acetamide;

d. thermal decomposition of nitrogen-containing starting compounds, such as N-methyl formamide, sodium acetyl cyanamide, cyanoacetic acid, methyl cyanoformate, lysidine hydrochloride, ethyl dichloramine, dimethylethylphenylammonium cyanide, thioacetamide, diacetyl monoxime, acetaldoxime, diethyl amine and ethyl amine.

These well known processes of the prior art have been described in more detail in the co-pending U.S. patent application Ser. 591,550, filed June 30, 1975, now abandoned.

It has been known that methyl amine in a quartz or Pyrex glass vessel is decomposed at 550°–670° C to form HCN, hydrogen, methane and ammonia (Carter, et al., Soc. 1939, 501) while at 350° C it still is stable (P. H. Emmett, R. W. Harkness, J. Amer. Chem. Soc. 54 (1932) 545).

It has also been known that the thermal decomposition of methyl amine over activated SiO$_2$ proceeds according to the scheme $$CH_3NH_2 \rightleftharpoons HCN + 2H_2 \qquad (1)$$

(Lovas, Clark, J. Chem. Phys. 62 (1975) 1925).

It has further been reported that methyl amine in the presence of activated iron catalyst (0.24% K$_2$O, 1.05% Al$_2$O$_3$) as is used for the ammonia synthesis, decomposes at 250° C practically quantitatively into ammonia, hydrogen and carbon (Emmett, Harkness, loc.cit.) Therefore, it has not at all been known that substantial amounts of acetonitrile could be formed from methyl amine using particular reaction conditions and catalysts.

We have now surprisingly and quite unexpectedly discovered an entirely novel route to the acetonitrile synthesis which provides in an economically and commercially feasible process a very high conversion of methyl amine into acetonitrile.

In contrast to the known noncatalytic thermal decomposition (1), the herein disclosed reaction occurs in theory according to the scheme $$2 CH_3NH_2 \rightarrow CH_3CN + NH_3 + 2H_2 \qquad (2)$$

Moreover, we have also found that dimethyl amine and trimethyl amine can also be converted to acetonitrile using the herein disclosed reaction conditions of the process of invention. It may be that methyl amine also in these cases arises as an intermediate. The practical utility resides in using advantageously also mixtures of these amines. It is well known that such mixtures can result, for example, from the reaction of carbon monoxide, ammonia and hydrogen, or from the technical synthesis of methyl amine, starting with methanol and ammonia.

On principle, the reaction of invention is generally conducted in the gaseous phase by passing a feed stream comprising hydrogen and methyl amine, dimethyl amine and/or trimethylamine at higher temperatures over a catalyst containing a transition metal oxide in a reduced state, and separating the acetonitrile from the effluent product gases. The metal catalyst preferably is supported on a refractory carrier material.

In the feed stream, excess hydrogen should preferably be present with respect to the amine. In general, beside the acetonitrile, also ammonia, hydrogen and methane, and small amounts to traces of other by-products such as propionitrile and HCN, may be formed. We have found that the conversion of amine to acetonitrile increases with increasing hydrogen rate, whereas the formation of HCN, as mentioned above, is suppressed. By increasing the hydrogen rate, however, also the production of methane is larger. Using methyl amine as the starting component in the feed stream, the molar ratio of hydrogen/amine is at least 0.5 to 1 and preferably in the range above 1.5 to 1, say 2 – 15: 1, when best conversion of amine to acetonitrile is desired. A greater excess of hydrogen is not excluded, whereas smaller hydrogen rates drastically decrease the conversion.

Moreover, we have found that especially on using trimethyl amine, the excess hydrogen inhibits practically the formation of propionitrile as a by-product. Useful catalysts for the process of this invention comprise at least one transition metal oxide which has been activated, i.e., subjected to a reductive treatment at elevated temperature. While these catalysts comprising these metal oxides in a certain reduced valency state exhibit different degrees of effectiveness when used per se, they generally possess additional catalytic activity when used in conjunction with well known refractory catalyst supports, such as dehydrated silicic acid, i.e., dehydrated silica gel, commonly also denoted active silica; or SiO$_2$; moreover, silica-alumina, silica-magnesia or zeolitic material, commonly termed molecular sieves. But other support materials such as alumina, thoria, magnesia, pumice, bentonite, bauxite, diatomaceous earth, silicon carbide, porcelain, kaolin, asbestos, slate, and the like, may also be used.

Under the term "transition metal" as used herein is understood any metal having partly filled $d$ or $f$ shells in any of their commonly occurring oxidation states.

In general, the catalysts contemplated herein are prepared by a process involving the following principal steps:

1. Providing a carrier with the desired decomposable metal salt or metal complex;
2. subjecting said carrier at elevated temperature to oxidizing conditions, e.g., by treating with air or oxygen at elevated temperature to convert the decomposable or oxidizable metal compound into the corresponding metal oxide; and
3. activating the resulting catalyst precursor under reducing conditions, e.g., by treating with hydrogen and/or ammonia, at elevated temperature to obtain the efficient catalyst having the transition metal oxide in a certain reduced valency state.

Under the term "decomposable or oxidizable transition metal compounds" as employed herein are understood those, which upon heating at suitable temperatures, e.g. 400°–600° C, or possibly up to 800° C, in an oxygen atmosphere are converted at least partially to the corresponding oxides by decomposition and/or replacement of their nonmetallic constituent by oxygen. Such nonmetallic constituents, in general, are parts of a transition metal salt, such as carbonate, nitrate, carboxylate (formate, acetate, oxalate, etc.) and the like, or parts of a transition metal complex, such as carbonyl, ammonium and the like.

Under the term "reducible transition metal compounds" as employed herein are understood those, in which can by heating at for example 400°–600° C., in a hydrogen and/or ammonia atmosphere, have their metallic constituent converted at least partially to a lower valency state and/or into a nitride. Such compounds are, for example, the transition metal oxides as obtained by the oxidation step (2) described above.

In the case where the carrier is already provided with a metal compound which is reducible according to the procedure of step (3), the preceding conversion to a reducible metal oxide may be omitted. Such cases are clear and predictable by those skilled in the art. The reduction may also be achieved by known chemical or electrochemical methods in liquid phase.

The active component precursors of the catalysts can be deposited on the carrier in accordance with known standard procedures, for example, by evaporating an aqueous solution containing an appropriate amount of the desired decomposable transition metal compound, e.g., a nitrate, such as ferric nitrate, or an ammonium complex, such as ammonium molybdate, jointly with a suspension or a paste of the carrier material. Alternatively, a carrier may be impregnated with a relatively more concentrated solution of the active catalyst precursor and then be filtered off or centrifuged. In another method, a carrier precursor, e.g., sodium silicate ($Na_2O \cdot xSiO_2$; $x = 3 - 5$), being dissolved in water, i.e., in the colloidal state (waterglass), is precipitated or rendered insoluble by adding an acid, such as chlorohydric acid, nitric acid, oxalic acid, etc., in the presence of the desired metal compound which may be dissolved or suspended. The obtained gel or co-gel is separated and/or dehydrated in common manner. Still another method is based on the precipitation by ammonia or alkali of a dissolved transition metal salt as a hydroxide, e.g., ferric or ferrous chloride as the corresponding iron hydroxides, in the presence of a suspended carrier. The resulting carrier having finely dispersed transition metal hydroxide thereon is filtered off or centrifuged and dried. It is understood that the catalyst precursors used in this invention can be prepared in any other ways besides those described above. Such methods are well known in the art.

The impregnated dry catalyst precursors bearing an appropriate quantity of decomposable transition metal compound are subsequently subjected to activation, i.e., to the oxidation step (2) and to the reduction step (3) as explained above. In the cases where the carrier is already provided with an appropriate metal oxide or hydrous metal oxide, e.g., $FeO$, $Fe_2O_3$, $Fe(OH)_3$, $Fe(OH)_2$, $Mo_2O_3$, $Mo_2O_5$, $PdO$, $PdO_2 \cdot xH_2O$, $VO_2$ $V_2O_5$, $V_2O_3$, $WO_2$, $W_2O_5$, $Ru(OH)_3$, $RuO_2$, and the like, the oxidative pretreatment according to step (2) may be omitted.

Transition metal hydrides and carbonyls also belong to the metal components which can directly be activated or used, respectively.

Comminuted minerals containing catalytically efficient quantities of transition metal component, such as hematite ($Fe_2O_3$), magnetite ($FeFe_3O_4$), siderite ($FeWO_4$), ferberite ($FeWO_4$), tungstenite (($Fe,MN)WO_4$), scheelite ($CaWO_4$), huebnerite ($MnWO_4$), manganite ($MnO(OH)$)$_2$, bunsenite ($NiO$), almandite ($Fe_3Al_2Si_3O_{12}$), bixbyite ($(Fe,Mn)_2O_3$), chromite ($FeCr_2O_4$), cuprite ($Cu_2O)_2$, powellite ($Ca(Mo,W)O_4$), wulfenite )$PbMoO_4$), etc. after oxidation and/or reduction can also successfully be employed. Combinations of synthetic catalysts and minerals, of course, are not excluded. The transition metals can also be combined. Particularly suited is a combination of molybdenum and chromium. Combinations of transition metal oxide and nontransition metal oxide, such as aluminium oxide, silicon oxide, boron oxide, antimony oxide, bismuth oxide, are also included because such oxides which are not reducible or difficulty reducible can serve as carrier or support as explained above.

The impregnated dry carrier catalyst precursors being preferably in the form of grains, spheres, cylinders, tablets, pellets, flakes, etc. and having convenient size are calcined, roasted or fired in an oxygen or air stream at a temperature high enough to decompose the metal compound and convert it to the corresponding metal oxide, but insufficient to substantially reduce the specific surface areas and the porosity as by too strong sintering or melting. In general, the oxidation temperature is preferably within the range of 400° to 600° C, where the oxidation may be accomplished in about 1 to 15 hours. This treatment is preferably followed by a purging treatment, such as passing a stream of inert gas, e.g., nitrogen, over the catalysts precursor.

The resulting catalyst precursor is subsequently activated, conditioned and stabilized by heating under reductive condition at a temperature sufficient for the reduction and for a time long enough to convert the metal oxide to a reduced state, which is considered to be the active metal species or its closest precursor. For example, the activation is satisfactorily achieved by heating the pretreated carrier and catalyst in a hydrogen atmosphere at 500° C for 3 to 10 hours.

The activation with ammonia is similarly performed, however, it generally takes longer, e.g., up to 40 hours at 500° C. A particularly efficient catalyst is obtained by reducing it first in a hydrogen atmosphere and then in an ammonia atmosphere as described above.

It is understood that the activation may also be carried out using a mixture of reducing gases. The activation at lower temperatures either does not occur or it takes unreasonably long. Those skilled in the art will recognize that the temperature and time will also depend on the type and the quantity of catalyst to be treated. The ability of the herein contemplated compounds to decompose or oxidize, respectively, can generally be predicted and are known to those skilled in the art.

Inasmuch as the catalyst precursor inevitably becomes also conditioned during the initial stages of the process, the operation may be dispensed with, since hydrogen is passed through at elevated temperature and ammonia is formed by decomposition of methyl amine reactant. The nature of actually active metal species has not yet been clarified and it is assumed that the reduced metal oxides may at least partially also be hydrided and/or nitrided.

When after a certain operation period the catalyst may become fouled which will affect the efficiency of the catalyst to decline to a point where further operation would be uneconomical, the catalyst can be regenerated by subjecting it to oxidation and subsequent reduction as before, i.e., the steps (2) and (3) are repeated.

The reactants used herein for the production acetonitrile are methyl amine, dimethyl amine and trimethyl amine, as well as hydrogen. The feed stream can also contain an inert gas such as nitrogen as a diluent.

In carrying out this process, the feed gases by be premixed and pre-heated, or may be separately charged to the reaction zone which is maintained at the desired reaction temperature. The reaction zone may be made of any material which is resistant to attack by the reactants or reaction products. Refractory and corrosion-resistant materials which may be used are stainless steel, porcelain, ceramics, high-silica glass, and quartz.

The reaction zone may be heated externally and/or internally by electrical means, including resistance heaters and induction heaters, or by combustion gases applied externally. The reaction zone may also be heated by combustion gases applied to heating tubes extending through the reactor.

The reactor may contain a fixed, a flowing, or a fluidized catalyst bed through which the reactant gas mixture is passed. The bed may also consist of a series of subsequent different sections, each containing a different catalyst and/or being operated at a different temperature. The different sections may then be adapted to particular performances. Since in the reaction of invention also ammonia and hydrogen are formed or preserved, respectively, these components may be brought to further reaction in a subsequent reaction zone In order to better accomplish such divided operations, the different sections each may be provided with inlets and outlets.

The reaction temperature is generally, at least, about 300°-350° C and preferably in the range of from about 400° to about 500° C. We have discovered that, e.g. a molybdenum on silica catalyst as described below is able to convert about 70% of methyl amine to acetonitrile per pass using a hydrogen/methyl amine ratio of about 12 and a reaction temperature of about 500° C.

It has already been stated and from the following Table it is apparent that on using this catalyst at 500° C excess hydrogen favors the optimum conversion amine → acetonitrile. However, also formation of methane increases and therefore the selectivity decreases. Accordingly, the criteria for determining the optimum temperature to be employed in any particular case will depend on a consideration of commercial feasibility from the standpoint of striking a practical balance between conversion, selectivity and losses to by-products. The reactant gases in this process may be passed through the reaction zone at a gaseous hourly velocity of approximately 50 to 15,000 or more. The space velocity is herein defined as the ratio of the volume of gases at standard temperature and pressure charged per hour to the volume of the reaction space. We prefer a space velocity of about 50 to 2,000. The reaction, contact or stay time, i.e., the period during which a unit volume of the reactants is in contact with a unit volume of catalyst, may vary between about a fraction of a second and several minutes. In general, a contact time varying between about 0.05 and about 60 seconds, preferably between about 0.1 and 20 seconds, gives satisfactory results. However, a flowing catalyst bed, in dependence of its grain size and/or bulk density, should preferably be charged at the catalyst discharge limit so that a relatively small quantity of the catalyst is discharged. It is understood, that in this instance the contact time can only be modified by varying the height of the flowing bed or by diluting the feed gas mixture appropriately with an inert gas, e.g., nitrogen. The residence time of the gas mixture in the reaction vessel containing the flowing bed consequently is not an independent variable. The stay time, for example, may be within the range of 0.2 to 50 seconds, preferably 0.5 to 20 seconds, and the apparent flow speed of the gaseous mixture in the reaction zone may be in the range of 50 to 150 cm per second.

The process of the present invention proceed well at atmospheric pressure. For example, with a catalyst containing 4.6% molybdenum (calculated as metal) on active silica, and employing a hydrogen/methyl amine ratio of about 12, a space velocity of about 230, a temperature of 500° C and atmospheric pressure, a conversion of methyl amines and a selectivity to acetonitrile of 70% or more can be reached.

In many instances, the yield and/or conversion to acetonitrile of the methyl amine to acetonitrile is associated with an excellent utilization of the active metal component of the catalyst. When the yield based on the metal content of the catalyst is calculated as follows $$\frac{\text{Quantity of Acetonitrile formed (kg)}}{\text{Quantity of Metal (kg)} \times \text{Time (hr)}}$$

to define the activity of the catalyst metal component, for example, with a catalyst of the above example, a production of 17.5 kg of acetonitrile per kg of molybdenum per hour can be realized, and this production can be maintained for many hours.

The reaction of invention can also be conducted at subatmospheric or superatmospheric pressure. Elevated pressures are insofar advantageous as they permit a greater throughput of the reactants and the condensation of the acetonitrile is more readily achieved. In general, a pressure within the range of 0.5 to 20 atmosphere (absolute), preferably 1 to 10 atmosphere (absolute) can be applied with satisfactory results. However, the reaction can also be conducted at higher pressure.

The reaction effluent may be complex. It generally comprises the desired acetonitrile, ammonia, hydrogen, hydrocarbons, and traces to small amounts of propionitrile and hydrocyanic acid. For the product separation, the effluent gases are cooled to a temperature sufficiently low to condense the acetonitrile, that is, below about 81° C.

EXAMPLE 1

Preparation of the Catalysts

Iron Catalyst

For the preparation of an iron catalyst according to the invention, 159, 6 g $Fe(NO_3)_3 \cdot 9H_2O$ are dissolved in 200 ml of water. To this solution are added 200 g of active silica (E. Merck, Darmstadt) in the form of grains having a diameter of about 0.2 to 0.5 mm (30 to 70 mesh ASTM) and the mixture is stirred for one hour. The remaining liquid is filtered and the residue dried in a rotary evaporator. The resulting catalyst precursor, after having been flushed with nitrogen, is heated under an oxygen stream at 500° C for 8 hours. Analysis of the iron deposited on the silica gives a value of $4 \times 10^{-4}$ g atom Fe per g of catalyst, i.e., 2.23%. The resulting oxidized catalyst precursor is activated by heating under a hydrogen stream at 500° C for 3 hours, or under an a ammonia stream at 500° C for 15 hours, respectively. The reduced catalyst has a bulk density of 0.54 g/ml and shows ferromagnetic property.

Similarly, catalysts are prepared containing $0.64 \times 10^{-4}$ or $17.7 \times 10^{-4}$ g atoms of iron per g of catalyst, i.e., 0.36% or 9.88%, respectively. The same catalyst can also be obtained by heating them in an ammonia stream at 500° C for 40 hours.

Molybdenum Catalyst

For the preparation of a molybdenum catalyst according to the invention, 33 g of $(NH_4)_6Mo_7O_{24} \cdot 4H_2O$ are dissolved in 150 ml of water. To this solutions are added 150 g of active silica and the resulting mixture is treated as above to obtain a catalyst containing $4.8 \times 10^{-4}$ g atoms of Mo per g of catalyst, i.e., 4.6%.

Mixed Metal Catalysts

For the preparation of mixed metal catalysts, i.e., catalysts containing two or more different metal components on a support, an aqueous solution of two or more decomposable salts or complexes is used, or alternatively, the impregnation is repeated after the oxidation step, using a different metal salt or complex than in the first impregnation. The subsequent activation or reduction is conducted as above.

Precipitated Iron Catalyst

To a suspension of 100g active silica in a solution of 730 g $Fe(NO_3)_3 \cdot 9H_2O$ in 1.5 liter of water is added with stirring a solution of 300 g of KOH in 1.5 liter of water. After filtering washing and drying, the catalyst precursor is oxidized with oxygen at 500° C during 6 hours, and then activated with $NH_3$ at 500° C during 3 – 15 hours.

EXAMPLE 2

In order to demonstrate a mode of carrying out the invention, the apparatus shown in the drawing is used.

A mixture of methyl amine and hydrogen is passed through an electrically heated Pyrex glass tube system comprising essentially two sections or compartments, namely a first section 1 being the premixer and preheater of the feed gases and a second section 2 being the reaction zone. An ordinary laboratory spiral cooler is used as the first section, having a jacket length of 154 mm and outside diameter of 26 mm, and a spiral tube 3 to 10 – 12 windings and inside diameter of 5 mm. The preheater 1 is connected with the reactor 2 through a straight tube 4, having a length of about 300 mm and inside diameter of 18 mm. The reactor, having a length of 300 mm and outside diameter of 26 mm is provided at its inlet with a glass fritte 5 and at the outlet with glass wool 6 to keep there between a fixed catalyst bed of 60 ml volumetric space. An inlet 7 for a thermoelement is arranged in the middle of the reactor for the temperature control. The preheater, the connection tube, the reactor and the outlet tube 8, totalizing a length of about 800 mm are disposed in an electric furnace as shown in the FIGURE by the dotted line.

The feed gases are introduced via rotameters through separate inlets 9, 10, 11 into the mixing chamber 12, having a volumetric capacity of about 30 ml and pass further through the glass tube system, being heated to the desired temperature.

The desired temperature and gas flow ratios are adjusted. A threeway valve (not shown) on the outlet 8 allows periodic removal of gas samples which are injected into two different gas chromatographs. The injections are repeated every 30 minutes until constant values are obtained. Temperatures, space velocities, reactant ratios and the type and quantity of the catalysts are then varied as indicated in Table I.

The selectivity to acetonitrile or conversion amine acetonitrile in the Table is determined as the percentage of reacted methyl amine that is found as acetonitrile (AcN):

$$\text{Selectivity to AcN} = \frac{2 \text{ AcN}}{2 \text{ AcN} + \text{CH}_4} \times 100$$

A. Mode of operation (not in accordance with this invention)

$4 \times 10^{-3}$ mol/min of methyl amine and $4.7 \times 10^{-3}$ mol/min of hydrogen are passed at 500° C over active silica. The analysis of the effluent product gases yields acetonitrile, ammonium cyanide, methane and other unidentified compounds. 3% of the carbon atoms introduced as methyl amine are present as acetonitrile in the effluent.

B. Mode of operation (not in accordance with this invention)

$4 \times 10^{-3}$ mol/min of methyl amine are passed at 500° C over active silica (same commercial grade as above), containing $0.48 \times 10^{-3}$ g atom of molybdenum per g of catalyst. The catalyst precursor has been treated and activated as described before in order to convert the original Mo(VI) to a lower valency state. The analysis of the effluent product gases yields acetonitrile, methane, ammonium cyanide, hydrogen and unidentified other compounds in lower concentrations. 10% of the carbon atoms introduced as methyl amine are present as acetonitrile and 7.5% as hydrocarbons, mainly $CH_4$.

C. Mode of operation (in accordance with this invention)

(1) $4 \times 10^{-3}$ mol/min of methyl amine and $9.6 \times 10^{-3}$ mol/min of hydrogen are passed at 500° C over the catalyst of example (B). The analysis of the effluent product gases yields as carbon-containing compounds acetonitrile, hydrocarbons, propionitrile and traces of unidentified other compounds. Methyl amine cannot be detected. About 53% of the carbon atoms introduced as methyl amine are present as acetonitrile and about 22% as hydrocarbons, mainly $CH_4$.

(2) $2.4 \times 10^{-3}$ mol/min of methyl amine and $9.6 \text{ mol} \times 10^{-3}$ mol/min of hydrogen are passed at 500° C over the catalyst of example (B). The analysis of the effluent product gases yields as carbon-containing compounds acetonitrile, hydrocarbons, propionitrile and traces of unidentified other compounds. No methyl amine is in the effluent. About 64% of the carbon atoms introduced as methyl amine are present as acetonitrile and about 16% as hydrocarbons, mainly methane.

(3) $0.8 \times 10^{-3}$ mol/min of methyl amine and $9.6 \times 10^{-3}$ mol/min of hydrogen are passed at 500° C over the catalyst of example (B). The analysis of the effluent product gases yields as carbon-containing compounds acetonitrile, hydrocarbons, propionitrile and traces of unidentified other compounds. Methyl amine is not present. About 70% of the carbon atoms introduced as methyl amine are present as acetonitrile and about 25% as hydrocarbons, mainly methane.

TABLE I

Dependence on $H_2$/amine ratio at various temperatures and flow speeds of the methyl amine
Catalyst: 4.6% Mo on $SiO_2$, activated with $NH_3$, 60 ml. volume

| Methyl Amine Flow Speed $10^3$ mol/min | Ratio $H_2$/Amine | Temperature °C | AcN in Effluent $10^3$ mol/min | Hydrocarbons in Effluent $10^3$ mol/min | Conversion % Amine→AcN |
|---|---|---|---|---|---|
| 4,0 | 0 | 400 | 0,09 | 0,15 | 4,5 |
| 4,0 | 0,6 | 400 | 0,20 | 0,12 | 10,0 |
| 4,0 | 1,2 | 400 | 0,24 | 0,16 | 12,0 |
| 4,0 | 0 | 500 | 0,21 | 0,30 | 10,5 |
| 4,0 | 0,6 | 500 | 0,40 | 0,49 | 20,0 |
| 4,0 | 1,2 | 500 | 0,62 | 0,59 | 31,0 |
| 4,0 | 2,4 | 500 | 1,07 | 0,90 | 53,5 |
| 2,4 | 4,0 | 500 | 0,77 | 0,38 | 64,1 |
| 1,6 | 6,0 | 500 | 0,51 | 0,27 | 63,7 |
| 0,8 | 12,0 | 500 | 0,28 | 0,20 | 70,0 |
| 4,0 | 1,2 | 400 | 0,03 | 0 1,5* | |
| 4,0 | 1,2 | 500 | 0,06 | 0,001 | 3,0 |

*Catalyst: $SiO_2$ without metal component

EXAMPLE 3

Methylamine was reacted over various metal catalysts under the conditions and with the results reported in Table II

TABLE II

| Ratio of Reactants: | $H_2/CH_3NH_2 = 12$ |
| Methylamine Feed: | $0.8 \times 10^{-3}$ mol/min |
| Catalyst: | $4.10 \times 10^{-4}$ g atom of metal on activated $SiO_2$ per g of catalyst |
| Reaction Temperature: | 500° C |

| | Conversion % | |
|---|---|---|
| Metal | $CH_3NH_2 \rightarrow CH_3CN$ | $CH_3NH_2 \rightarrow$ Hydrocarbons* |
| Mo | 70.0 | 25.0 |
| W | 60.0 | 29.0 |
| Cr | 55.0 | 11.2 |
| Ru | 50.0 | 6.0 |
| Fe | 25.0 | 75.0 |
| Ni | <0.01 | ≃ 100 |
| Co | <0.01 | ≃ 90 |

*mainly $CH_4$

EXAMPLE 4

Amines were reacted over a molybdenum catalyst under the conditions and with the results reported in Table III.

TABLE III

| Ratio of Reactants: | $H_2$/Amine = 12 |
| Amine Feed: | $0.8 \times 10^{-3}$ mol/min |
| Catalyst: | $4.8 \times 10^{-4}$ g atom of molybdenum on activated $SiO_2$ per g of catalyst |
| Reaction Temperature: | 500° C |

| | Conversion % | |
|---|---|---|
| Amine | Amine→ $CH_3CN$ | Amine→Hydrocarbons* |

TABLE III-continued

| $CH_3NH_2$ | 70 | 25 |
| $(CH_3)_2NH_2$ | 65 | 26 |
| $(CH_3)_3N$ | 58 | 27 |

*mainly $CH_4$

In a particular aspect, a new route from methyl amine, dimethyl amine and/or trimethyl amine and hydrogen to acrylonitrile is considered part of the present invention. The amines in the presence of hydrogen can be converted to acetonitrile by high temperature reaction, as over a transition metal catalyst as taught herein, and the acetonitrile can readily be converted to acrylonitrile by reaction with formaldehyde, as for example a vapor phase catalytic reaction of acetonitrile and formaldehyde as described, for example, in Snapp et al, U.S. Pat. No. 3,701,798, employing the rare earth metal oxide catalysts there described, of the lanthanide series, or the basic metal compounds there referred to, e.g. salts or oxides of alkali metals, lead, zinc, chromium, manganese, etc.

What is claimed is:

1. A process for preparing acetonitrile by contacting hydrogen and at least one of methylamine, dimethylamine and trimethylamine molar ratio of hydrogen to amine of at least 0.5 to 1 at an elevated temperature of at least about 300° C and sufficiently high to induce reaction with a catalytically effective amount of catalyst comprising a transition metal in a reduced valence state which renders it effective toward synthesis of acetonitrile, at a space velocity of about 50 to about 2000 reciprocal hours, and recovering acetonitrile.

2. The process of claim 1 in which the temperature is in the range of about 400° to 550° C.

3. The process of claim 1 in which the transition metal in reduced valence state has been formed by heating a reducible transition metal compound at 400°–600° C in a reducing atmosphere selected from hydrogen and ammonia and mixtures thereof for a time sufficient to reduce at least partially said transition metal compound.

4. The process of claim 1 in which the molar ratio of hydrogen to amine is at least 1.5.

5. The process of claim 1 in which the catalyst consists essentially of a Group VIII metal component.

6. The process according to claim 3 in which the reducible transition metal compound is a transition metal oxide.

7. The process of claim 1 in which the transition metal is molybdenum.

8. The process according to claim 1 characterized in that the carrier is active silica.

9. The process according to claim 6 characterized in that the transition metal oxide is iron oxide, molybdenum oxide, vanadium oxide or tungsten oxide.

10. The process according to claim 6 characterized in that the transition metal oxide has been prepared by impregnating the carrier with an oxidizable transition metal compound and heating it in an oxygen atmosphere at 400°–800° C, for 1–10 hours.

11. The process according to claim 10 characterized in that the oxidizable transition metal compound is $(NH_4)_6Mo_7O_{24}.4H_2O$.

12. The process according to claim 1 characterized in that the catalyst has been activated by heating with ammonia at 500° C for 1 – 10 hours.

13. The process according to claim 1 characterized in that the carrier contains 0.1 to 10% by weight of the transition metal compound, calculated as metal.

14. The process according to claim 1, characterized in that hydrogen, and methyl amine are brought into contact at 500° C in the presence of a catalyst which is a molybdenum compound on active silica, the molar ratio of the hydrogen to methyl amine being 12, and the catalyst has been prepared by heating $(NH_4)_6Mo_7O_{24}.4H_2O$ in an oxygen atmosphere at 500° C for 8 hours and subsequently in an ammonia atmosphere at 500° C for 16 hours, and acetonitrile is recovered by cooling the effluent product gases.

15. The process according to claim 14 characterized in that the silica contains 3 – 6% by weight of the molybdenum compound, calculated as metal.

16. The process according to claim 14, characterized in that the contact time of the methyl amine is about 40–60 seconds.

17. The process of claim 1 in which the temperature is in the range of about 400° to 550° C and molar range of hydrogen to amine in the range of 2 to 15:1, and the transition metal is on a refractory catalyst support.

18. The process of claim 17 in which the transition metal is selected from iron, molybdenum, vanadium, or tungsten.

19. The process of claim 17 in which the transition metal in reduced valence state has been formed by heating a reducible transition metal compound at 400°–600° C in a reducing atmosphere selected from hydrogen and ammonia and mixtures thereof for a time sufficient to reduce at least partially said transition metal compound.

20. The process according to claim 19 in which the reducible transition metal compound is selected from oxides of iron, molybdenum, vanadium or tungsten.

21. The process of claim 20 in which the reducible transition metal compound has been prepared by impregnating the carrier with an oxidizable transition metal compound and heating it in an oxygen atmosphere at 400°–800° C, for 1–10 hours.

22. The process of claim 19 in which the transition metal is molybdenum.

23. The process of claim 17 in which the support is alumina.

24. The process of claim 17 in which the pressure is in the range of 0.5 to 20 atmospheres.

* * * * *